(12) United States Patent
Lehr et al.

(10) Patent No.: US 8,981,145 B2
(45) Date of Patent: Mar. 17, 2015

(54) PROCESS FOR PREPARING ISOCYANATES

(75) Inventors: Vanessa Simone Lehr, Mannheim (DE); Torsten Mattke, Freinsheim (DE)

(73) Assignee: BASF SE, Ludwigshafen (DE)

( * ) Notice: Subject to any disclaimer, the term of this patent is extended or adjusted under 35 U.S.C. 154(b) by 264 days.

(21) Appl. No.: 13/050,194

(22) Filed: Mar. 17, 2011

(65) Prior Publication Data

US 2011/0230676 A1    Sep. 22, 2011

Related U.S. Application Data

(60) Provisional application No. 61/315,089, filed on Mar. 18, 2010.

(51) Int. Cl.
    *C07C 263/10* (2006.01)
(52) U.S. Cl.
    CPC .................................. *C07C 263/10* (2013.01)
    USPC ........................................... 560/347; 560/338
(58) Field of Classification Search
    USPC .................................................. 560/347, 338
    See application file for complete search history.

(56) References Cited

U.S. PATENT DOCUMENTS

| 4,847,408 | A | 7/1989 | Frosch et al. |
| 5,391,683 | A | 2/1995 | Joulak et al. |
| 5,449,818 | A | 9/1995 | Biskup et al. |
| 5,516,935 | A | 5/1996 | Bischof et al. |
| 5,633,396 | A | 5/1997 | Bischof et al. |
| 6,706,913 | B2 | 3/2004 | Leimkuhler et al. |
| 6,800,781 | B2 | 10/2004 | Herold et al. |
| 6,803,482 | B2 | 10/2004 | Jenne et al. |
| 6,838,578 | B2 | 1/2005 | Leimkuhler et al. |
| 7,019,164 | B2 | 3/2006 | Friedrich et al. |
| 7,084,297 | B2 * | 8/2006 | Woelfert et al. ............... 560/347 |
| 7,358,388 | B2 | 4/2008 | Woelfert et al. |
| 7,488,842 | B2 | 2/2009 | Knoesche et al. |
| 7,615,662 | B2 * | 11/2009 | Pohl et al. ....................... 560/347 |
| 8,716,517 | B2 | 5/2014 | Mattke et al. |
| 2005/0272910 | A1 | 12/2005 | Wolfert et al. |
| 2007/0015934 | A1 | 1/2007 | Wolfert et al. |
| 2009/0149672 | A1 | 6/2009 | Pohl et al. |
| 2010/0056822 | A1 | 3/2010 | Daiss et al. |
| 2010/0076218 | A1 | 3/2010 | Daiss et al. |
| 2010/0210870 | A1 | 8/2010 | Olbert et al. |
| 2010/0217035 | A1 | 8/2010 | Knoesche et al. |
| 2010/0305356 | A1 | 12/2010 | Olbert et al. |
| 2011/0213178 | A1 | 9/2011 | Mattke et al. |
| 2011/0257428 | A1 | 10/2011 | Knoesche et al. |
| 2011/0301380 | A1 | 12/2011 | Knoesche et al. |
| 2012/0004445 | A1 | 1/2012 | Lehr et al. |
| 2012/0004446 | A1 | 1/2012 | Mattke et al. |
| 2012/0016154 | A1 | 1/2012 | Mattke et al. |

FOREIGN PATENT DOCUMENTS

| DE | 10260092 A1 | 7/2004 |
| EP | 0289840 A1 | 11/1988 |
| EP | 570799 A1 | 11/1993 |
| EP | 593334 A1 | 4/1994 |
| EP | 669657 A2 | 8/1995 |
| EP | 749958 A1 | 12/1996 |
| EP | 1078918 A1 | 2/2001 |
| EP | 1275639 A1 | 1/2003 |
| EP | 1275640 A1 | 1/2003 |
| EP | 1319655 A2 | 6/2003 |
| EP | 1362847 A2 | 11/2003 |
| EP | 1403248 A1 | 3/2004 |
| EP | 1935875 A1 | 6/2008 |
| EP | 2062876 A1 | 5/2009 |
| EP | 09167604.9 | 2/2011 |
| WO | WO-03/045900 A1 | 6/2003 |
| WO | WO-2004/026813 A1 | 4/2004 |
| WO | WO-2005/123665 A1 | 12/2005 |
| WO | WO-2008/055899 A1 | 5/2008 |
| WO | WO-2008/055904 A1 | 5/2008 |
| WO | WO-2008/086922 A1 | 7/2008 |
| WO | WO-2009/027232 A1 | 3/2009 |
| WO | WO-2009/027234 A1 | 3/2009 |
| WO | WO-2009/037179 A1 | 3/2009 |
| WO | WO-2010/010135 A1 | 1/2010 |
| WO | WO-2010/043532 A1 | 4/2010 |
| WO | WO-2010/052230 A2 | 5/2010 |
| WO | WO-2010/063665 A1 | 6/2010 |
| WO | WO-2010/100221 A1 | 9/2010 |
| WO | WO-2010/106131 A2 | 9/2010 |
| WO | WO-2010/115908 A2 | 10/2010 |
| WO | WO-2011/018443 A2 | 2/2011 |
| WO | WO-2011/104264 A1 | 9/2011 |

OTHER PUBLICATIONS

Fichtner et al; Proceedings of the International Conference on Heat transfer and Transport Phenomena in Microscale, Oct. 2000, 41-53.*
U.S. Appl. No. 13/001,681, filed Dec. 28, 2010, Carsten Knoesche et al.
U.S. Appl. No. 13/057,869, filed Feb. 7, 2011, Ulrich Penzel et al.

* cited by examiner

*Primary Examiner* — Sudhakar Katakam
*Assistant Examiner* — Pancham Bakshi
(74) *Attorney, Agent, or Firm* — Drinker Biddle & Reath LLP

(57) ABSTRACT

The invention relates to a process for preparing isocyanates, comprising (a) the reaction of at least one amine with phosgene in the gas phase in a reaction zone and (b) the subsequent cooling of the reaction gases in a cooling zone by means of indirect cooling, the cooling medium which absorbs the heat of the reaction gases being conducted in countercurrent to the product stream at least in the region of the highest temperature in the cooling zone.

19 Claims, 1 Drawing Sheet

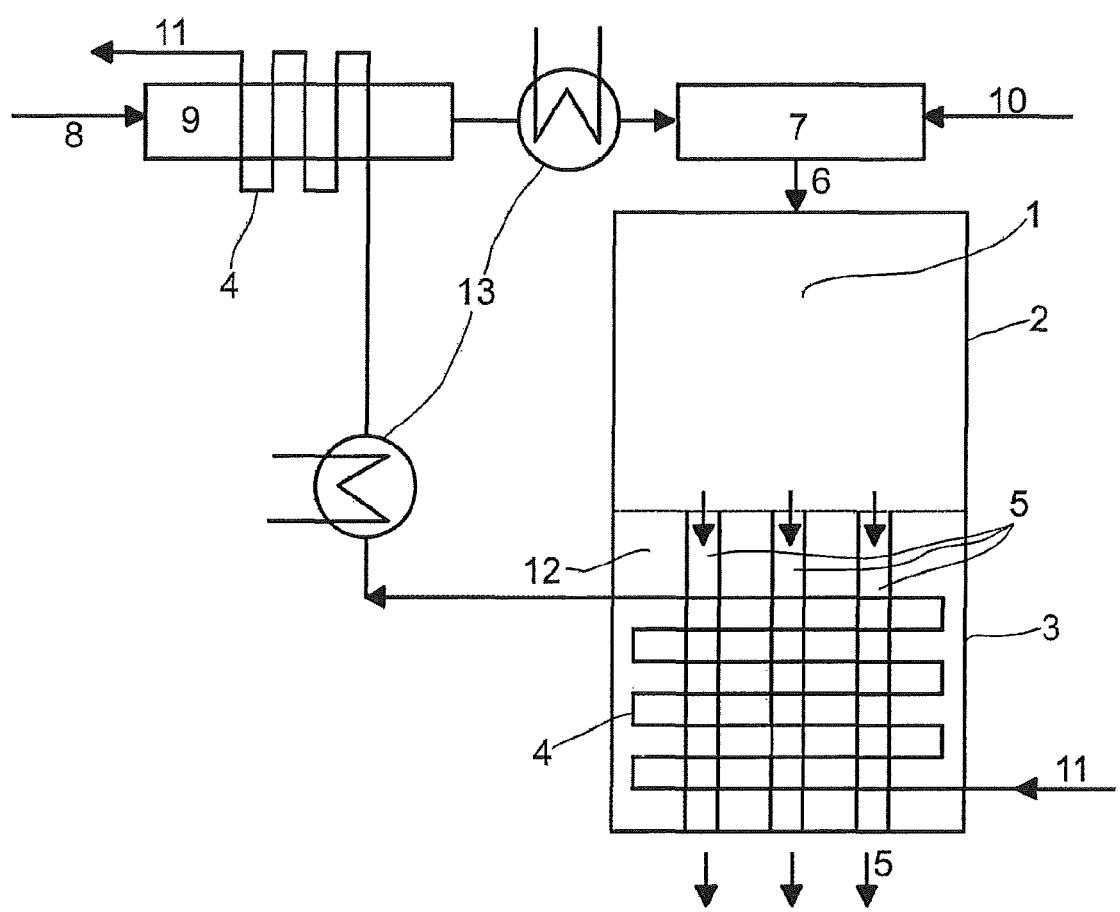

PROCESS FOR PREPARING ISOCYANATES

CROSS-REFERENCE TO RELATED APPLICATIONS

This Application claims the benefit of U.S. Provisional Application 61/315,089 filed Mar. 18, 2010, the contents of which are incorporated herein by reference in its entirety.

FIELD OF THE INVENTION

The invention relates to a process for preparing isocyanates, comprising (a) the reaction of at least one amine with phosgene in the gas phase in a reaction zone and (b) the subsequent cooling of the reaction gases in a cooling zone by means of indirect cooling, the cooling medium which absorbs the heat of the reaction gases being conducted in countercurrent to the product stream at least in the region of the highest temperature in the cooling zone.

BACKGROUND OF THE INVENTION

Isocyanates, especially diisocyanates, are prepared predominantly by phosgenating the corresponding amines. The phosgenation can be performed either in the liquid phase or in the gas phase. In industrial implementation, gas phase phosgenation has a series of advantages over liquid phase phosgenation, especially a higher selectivity, a lower holdup of toxic phosgene, and lower capital and energy costs.

The phosgenation of amines to isocyanates in the gas phase is known per se, for example from EP-A 570 799, EP-A 749 958 and EP-A 1 078 918. This involves evaporating one amine-containing and one phosgene-containing reactant stream, if they are not already in the gas phase, and bringing them to the reaction temperature of the gas phase phosgenation, for example of about 300 to 400° C. The provision of the high-temperature heat according to the known processes is very costly.

The gaseous product stream has to be cooled after the reaction. It is known from the prior art that the reaction gases have to be cooled rapidly in order to very substantially avoid the formation of undesired conversion products. In the prior art, what is known as quenching is predominantly used for that purpose. Quenching involves cooling by means of direct contact with a cooling liquid, which is preferably sprayed into the stream of the hot reaction gases, as described, for example, in EP-A 1 403 248. This ensures rapid cooling, i.e. a short cooling time, such that the undesired formation of conversion products can be substantially prevented.

EP-A 1 935 875 discloses, for example, a process for preparing isocyanates in the gas phase, in which the reaction is stopped by conducting the reaction mixture out of the reaction chamber through a cooling zone into which liquids are sprayed, such that the reaction gases are cooled directly. According to this published specification, indirect cooling by means of heat exchangers is disadvantageous owing to the poor heat transfer and also leads to the formation of deposits of solids on the comparatively cold surfaces of the heat exchangers as a result of side reactions of the gas mixture on these surfaces. To avoid these disadvantages, EP-A 1 935 875 proposes direct cooling by means of quenching.

However, the cooling processes known from the prior art, owing to the rapid cooling of the reaction gases and the high temperature differences from the heat-absorbing medium, especially in the course of quenching, often result in undesired aerosol formation. Aerosols formed can be removed again only with difficulty by conventional industrial processes and increase the complexity of the further workup to purify the individual components.

Furthermore, the waste heat which is absorbed by heating or evaporation of the quench liquid in the direct cooling processes of the prior art can be utilized only at a relatively low temperature level. When indirect heat transferers are utilized, further utilization of the waste heat is possible in principle. In this case, it would be desirable to heat the heat carrier medium, which absorbs the heat, to such an extent that a high temperature level is attained, which ideally corresponds completely or approximately to the temperature of the reactant streams used in the reaction zone or to the evaporation temperature of one or more reactants. This could allow the heat to be stored at a high temperature level. This enables universal reuse of the waste heat in the process.

BRIEF SUMMARY OF THE INVENTION

It was therefore an object of the invention to provide a process for preparing mono- and/or diisocyanates by gas phase phosgenation of the corresponding amines, which has the aforementioned disadvantages to a lesser degree, if at all.

More particularly, the formation of conversion products should be avoided. In addition, the energy transferred to the cooling medium should be kept at a maximum temperature level. Furthermore, the formation of aerosols in the cooling zone should be avoided.

The aforementioned objects are achieved by the process according to the invention. Preferred embodiments can be inferred from the claims and the description which follows. Combinations of preferred embodiments do not leave the scope of the present invention.

DETAILED DESCRIPTION OF THE PREFERRED EMBODIMENTS

The process according to the invention for preparing isocyanates comprises at least the following steps:
(a) the reaction of at least one amine with phosgene in the gas phase in a reaction zone and
(b) the subsequent cooling of the reaction gases in a cooling zone by means of indirect cooling, the cooling medium which absorbs the heat of the reaction gases being conducted in countercurrent to the product stream at least in the region of the highest temperature in the cooling zone.

The individual steps of the process according to the invention are explained hereinafter.

Step (a)

"Reaction zone" is understood to mean the region within the reactor in which the reaction in step (a) proceeds. The region or the point at which the conversion of the starting compounds and intermediates according to the present stoichiometry and reaction kinetics is essentially complete indicates the end of the reaction zone (in terms of space) and the end of the conversion (for reaction purposes). The conversion of the starting compounds is essentially complete when the formation of at least 90% by weight, preferably at least 95% by weight, especially at least 99% by weight, of the isocyanate prepared by the process or the corresponding carbamoyl chlorides is complete.

In the process according to the invention, phosgene is reacted with at least one amine in the gas phase. It is known to those skilled in the art that the formation of the isocyanates proceeds via intermediates. Intermediates are, for example, the mono-aminomonocarbamoyl chlorides, dicarbamoyl chlorides, monoaminomonoisocyanates and monoisocyanatomonocarbamoyl chlorides formed from the diamines, and the hydrochlorides of the amino compounds.

"Conversion in the gas phase" is understood to mean that the reactants and intermediates react with one another in the gaseous state and, in the course of the reaction, during passage through the reaction zone, remain in the gas phase to an extent of at least 95% by weight, preferably to an extent of at least 98% by weight, more preferably to an extent of at least 99% by weight, even more preferably to an extent of at least 99.5% by weight, especially to an extent of at least 99.9% by weight.

Furthermore, the invention is not restricted per se with regard to the specific performance of the reaction of amines with phosgene in the gas phase (step a). Corresponding implementations of the reaction of amines with phosgene in the gas phase according to step (a) are widely known to those skilled in the art and are described, for example, in EP-A 2 062 876 and in the documents cited there. The present invention can thus be integrated into known processes for preparing isocyanates by phosgenating amines in the gas phase.

Preferred implementations of the inventive conversion in step (a) are described, for example, in WO 2009/027232, WO 2009/037179, WO 2008/086922, EP-A 09167604.9, WO 2010/010135 and WO 2009/027234, the content of each of which is hereby explicitly incorporated by reference, except that the cooling described in the documents cited should be replaced in each case by the inventive cooling (b).

The reaction of the amines, especially diamines, with phosgene is preferably performed in stoichiometric excess, such that the amines are used in stoichiometric deficiency in relation to phosgene. Typically, a molar ratio of phosgene to reactive amino groups of 1.1:1 to 20:1, preferably of 1.2:1 to 10:1, is present.

The reactant stream comprising amines comprises the amines corresponding to the desired isocyanate target product. For the process according to the invention, the amines used for reaction to give the corresponding isocyanates may be those which can be converted to the gas phase without significant decomposition, i.e. undecomposed to an extent of at least 95% by weight, preferably undecomposed to an extent of at least 98%, more preferably to an extent of at least 99%, even more preferably to an extent of at least 99.5%, particularly to an extent of at least 99.8%, especially to an extent of at least 99.9% and even to an extent of at least 99.95% by weight. It is possible to use aliphatic, cycloaliphatic or aromatic amines, preferably aliphatic or aromatic amines. Diamines are preferred as amines. Isocyanates which can be prepared by the process according to the invention may accordingly be aromatic, cycloaliphatic or aliphatic isocyanates, preference being given to diisocyanates.

Particular preference is given to amines, especially diamines, based on aromatic hydrocarbons having from 6 to 18 carbon atoms, and those based on aliphatic or cycloaliphatic hydrocarbons having 2 to 18 carbon atoms. Preferred (cyclo)aliphatic amines derive from the (cyclo)aliphatic isocyanates detailed hereinafter. In the context of this application, (cyclo)aliphatic isocyanates is an abbreviated notation for cycloaliphatic and/or aliphatic isocyanates.

Reference is made hereinafter to the isocyanates obtainable with preference. The amines correspondingly used with preference according to the present invention are those which derive from the isocyanates mentioned hereinafter by replacement of the isocyanate groups with primary amine groups.

Cycloaliphatic isocyanates are those which comprise at least one cycloaliphatic ring system.

Aliphatic isocyanates are those which have exclusively isocyanate groups which are bonded to straight or branched chains. These may also comprise aromatic ring systems, provided that isocyanate groups are not bonded to them.

Aromatic isocyanates are those which have at least one isocyanate group bonded to at least one aromatic ring system.

Preferred aromatic isocyanates comprise from 6 to 20 carbon atoms. Especially preferred is monomeric methylene di(phenyl isocyanate), also known as diisocyanatodiphenylmethane and abbreviated to MDI, especially 4,4'-diisocyanatodiphenylmethane, 2,4'-diisocyanatodiphenylmethane and/or 2,2'-diisocyanatodiphenylmethane, and also 2,4- and/or 2,6-tolylene diisocyanate (TDI) and naphthyl diisocyanate (NDI).

Preferred (cyclo)aliphatic diisocyanates are the aliphatic isocyanates tetramethylene diisocyanate, pentamethylene diisocyanate (1,5-diisocyanatopentane), hexamethylene diisocyanate (1,6-diisocyanatohexane), 2-methylpentane 1,5-diisocyanate, 1,8-octa-methylene diisocyanate, 1,10-decamethylene diisocyanate, 1,12-dodecamethylene diisocyanate, 1,14-tetradecamethylene diisocyanate, derivatives of lysine diisocyanate, tetramethylxylylene diisocyanate (TMXDI), trimethylhexane diisocyanate or tetra-methylhexane diisocyanate, and also 3 (or 4), 8 (or 9)-bis(isocyanatomethyl)tricyclo-[5.2.1,0$^{2,5}$]decane isomer mixtures, and also the cycloaliphatic diisocyanates 1,4-, 1,3- or 1,2-diisocyanatocyclohexane, 4,4'- or 2,4'-di(isocyanatocyclohexyl)methane, 1-isocyanato-3,3,5-trimethyl-5-(isocyanatomethyl)cyclohexane (isophorone diisocyanate), 1,3- or 1,4-bis (isocyanatomethyl)cyclohexane, 2,4- or 2,6-diisocyanato-1-methylcyclohexane.

Particular preference is given to 1,6-diisocyanatohexane, 1-isocyanato-3,3,5-trimethyl-5-(isocyanatomethyl)cyclohexane, 4,4'-di(isocyanatocyclohexyl)methane and tolylene diisocyanate isomer mixtures.

Apart from diisocyanates, it is also possible in principle by the process according to the invention to obtain monoisocyanates with one isocyanate group or higher isocyanates with an average of more than 2 isocyanate groups. Suitable examples for this purpose are triisocyanates such as triisocyanatononane, 2,4,6-triisocyanatotoluene, triphenyl-methane triisocyanate or 2,4,4'-triisocyanatodiphenyl ether, or the mixtures of diisocyanates, triisocyanates and higher polyisocyanates which are obtained, for example, by phosgenation of appropriate aniline/formaldehyde condensates, and polyphenyl polyisocyanates having methylene bridges.

A preferred monoisocyanate is phenyl isocyanate. Preference is given, however, to the preparation of diisocyanates. Very particular preference is given in the context of the present invention to obtaining tolylene diisocyanate (TDI), especially 2,4- and/or 2,6-tolylene diisocyanate.

In the case of phosgenation in the gas phase, the aim is that all compounds which occur in the course of reaction, i.e. reactants (amine and phosgene), intermediates (especially the mono- and dicarbamoyl chlorides which form as intermediates), end products (isocyanate, hydrogen chloride), and any inert medium metered in, remain in the gas phase under the reaction conditions within the at least one reaction zone. The reactants, the inerts or reactant-inert gas mixture are/is preferably already present completely in the gaseous phase upstream of the reaction zone.

This means that the gas stream does not comprise any droplets of unevaporated amine, and condensation processes on the path between evaporation and mixing nozzle up to the conclusion of the reaction zone are prevented by suitable measures.

Droplet formation can be prevented especially by superheating the streams, and further technical measures known to those skilled in the art for preventing condensation at cold sites. The reactants or reactant-inert gas mixtures are more preferably already superheated upstream of the reaction zone. "Superheated" means that the reactant mixtures are heated above the boiling point which arises at the particular pressure. This superheating is effected to temperatures which are within the range specified for the reaction zone.

Should the reactants or the intermediates which form in the course of the reaction or the target products separate out of the gas phase, for example on the reactor wall or other apparatus components, these depositions can undesirably alter the heat transfer or the flow through the components affected.

At the start of step (a), the amine preferably has a temperature in the range from 200 to 450° C. The pressure of the amine added is preferably in the range between 0.05 and 5 bar absolute. The temperature of the phosgene added is preferably in the range from 250 to 450° C. For this purpose, the phosgene is typically heated before addition in a manner known to those skilled in the art. The two reactant streams, i.e. the reactant stream comprising the amine and the phosgene-comprising reactant stream, are more preferably preheated to a temperature in the range from approx. 300 to 450° C. and hence used at this temperature in step (a).

Prior to step (a), at least one stream comprising gaseous phosgene is preferably mixed with at least one stream comprising gaseous amine, and then this mixture is converted in step (a) at a temperature of 200 to 600° C. in the at least one reaction zone.

The amine-containing reactant stream can be heated to reaction temperature in more than one stage. Various heat sources can be used. The heat sources available include customary sources such as steam, electrical heating and combustion gases. In addition, the heat absorbed by the cooling medium in the course of step (b) can advantageously be utilized at least partly for indirect heat transfer to at least one reactant stream of the reaction in step (a), especially to the amine-containing reactant stream.

The transfer of heat to the amine-containing reactant stream is effected in principle by indirect heat transfer. Optionally, a separate heat carrier circuit is installed between heat source and amine-containing reactant stream. Suitable heat carriers are salt melts or other high-temperature heat carriers.

The heating of the amine-containing reactant stream comprises essentially heating up to the boiling temperature of the amine-containing reactant stream, the evaporation thereof and superheating thereof to the desired inlet temperature into the reaction zone. Each of these three steps can be carried out in one or more apparatuses with identical or different heat sources.

In a preferred embodiment, the amine-containing reactant stream is heated with steam in one or more apparatuses up to close to the condensation temperature of the steam or steam inlet temperature. Any amount of heat lacking up to the desired inlet temperature into the reaction zone, which is required for superheating and optionally evaporation (or heating up to evaporation temperature), is preferably provided from the heat absorbed by the cooling medium in step (b), optionally supplemented by heat from electrical heating or combustion gases. This can in turn be effected in a single apparatus or in a plurality of apparatuses.

Useful apparatus types for preheating the reactant streams are those known to the person skilled in the art. For preheating or superheating, it is possible to use especially tube bundle heat exchangers, plate heat exchangers and analogous heat exchangers known to those skilled in the art.

The evaporation can be performed in customary evaporator types such as circulation evaporators, falling-film evaporators, climbing-film evaporators, thin-film evaporators, milli- or microevaporators. To prevent decomposition, the evaporation can be performed at lower pressures and therefore lower boiling temperatures. Any required compression to the reaction pressure can be implemented by suitable compressor constructions or by use of an ejector nozzle as a mixing device.

For the phosgene-containing reactant stream, essentially that written above for the amine-containing reactant stream applies. It may, however, be the case that the phosgene stream provided is already in gaseous form and hence no evaporation is required. Under some circumstances, a liquid phosgene-containing reactant stream may still comprise portions of a relatively high-boiling solvent which are undesired in the reaction zone. In this case, this reactant stream can be partly evaporated, in which case the solvent-depleted gas stream, optionally superheated further, serves as a reactant stream for the reaction. The remaining solvent-enriched stream can be sent to a suitable workup.

Both the phosgene and the reactant stream comprising the amine can each be diluted with an inert gas, i.e. an additional inert medium can be added to the phosgene stream and/or amine stream in the context of the present invention. The inert medium is a medium which is essentially in gaseous form in the reaction chamber at the reaction temperature and essentially does not react with the compounds which occur in the course of the reaction or is stable under the reaction conditions. Preference is given to those inert media which remain undecomposed and unreacted to an extent of at least 95% by weight under the reaction conditions, preferably to an extent of at least 98%, more preferably to an extent of at least 99%, even more preferably to an extent of at least 99.5% and especially to an extent of at least 99.9% by weight.

The inert medium is generally mixed with the amine and/or phosgene before the reaction or may already be part of the recycled phosgene, but may also be metered separately from the reactant streams, for example, directly into the reaction zone. For example, it is possible to use nitrogen, carbon dioxide or carbon monoxide, noble gases such as helium or argon, or aromatics such as toluene or xylene, or chlorinated aromatics such as chlorobenzene or dichlorobenzene. Preference is given to using nitrogen and/or chlorobenzene as the inert medium.

In general, the inert medium is used in such an amount that the ratio of the gas volumes of inert medium to amine and/or to phosgene is more than 0.0001 to 30, preferably more than 0.001 to 15, more preferably more than 0.001 to 5.

The supply of phosgene via the phosgene-containing stream to the reaction chamber can also be effected in such a way that a plurality of phosgene-containing substreams are supplied instead of a single phosgene-containing stream. In such a case, the phosgene-containing substreams are added up to give a phosgene-containing overall stream.

In one possible embodiment, the phosgene used and/or the phosgene recycled in the process is not supplied directly to the reaction zone, but first to a phosgene purification. This may be advisable especially in order to remove traces of molecular chlorine there, and so this embodiment is especially preferred when the phosgene obtained from the phosgene synthesis still comprises traces of molecular chlorine ($Cl_2$), for example at a content of more than 5 ppm, preferably at more than 3 ppm, more preferably at more than 1 ppm, even more preferably at more than 0.5 ppm and especially at a content of more than 0.1 ppm.

The reactants are preferably mixed in a mixing apparatus which preferably features a high shear of the reaction streams conducted through the mixing apparatus. The mixing apparatus used is preferably a static mixing apparatus such as a mixing nozzle, which is positioned upstream of the reaction zone according to step (a) of the process according to the invention. Particular preference is given to using a mixing nozzle.

The mixing can be effected by different measures, especially as described in EP-A 699 657, EP-A 1 319 655, column 1 line 54 to column 2 line 24 and column 4 lines 16 to 40, EP-A 1 275 640, column 3 line 27 to column 4 line 5, EP-A 1 362 847, column 2 line 19 to column 3 line 51 and column 4 line 40 to column 5 line 12, and WO 2010/010135, explicit reference being made to each of these in the context of this disclosure.

After the mixing in the mixing apparatus, the gaseous mixture of phosgene, amine and optionally inert medium is conducted into the reactor, the reactor comprising the reaction zone.

"Reactor" is understood to mean the industrial apparatus which comprises the reaction zone. In step (a), useful reactors are all customary reactors which are known from the prior art and are suitable for noncatalytic monophasic gas reaction, preferably for continuous noncatalytic monophasic gas reaction, and which withstand the pressures required. Suitable materials for contact with the reaction mixture are, for example, metals such as steel, especially alloyed steel, tantalum, nickel, nickel alloys, silver or copper, glass, ceramic, enamel, or homogeneous or heterogeneous mixtures and components thereof. Preference is given to using steel reactors. The walls of the reactor may be smooth or profiled. Suitable profiles are, for example, grooves or corrugations.

Corresponding reactor designs are known. Examples of suitable reactors are described in EP-B1 289 840, column 3 line 49-column 4 line 25, in EP-B1 593 334, WO 2004/026813, page 3 line 24-page 6 line 10, in WO 03/045900, page 3 line 34-page 6 line 15, in EP-A11 275 639, column 4 line 17-column 5 line 17, and in EP-B1 570 799, column 2 line 1-column 3 line 42, explicit reference being made to each of these in the context of this disclosure. Preference is given to using tubular reactors.

It is likewise possible to use essentially cuboidal reaction chambers, preferably plate reactors or plate reaction chambers. A particularly preferred plate reactor has a ratio of width to height of at least 2:1, preferably at least 3:1, more preferably at least 5:1 and especially at least 10:1. The upper limit of the ratio of width to height depends on the desired capacity of the reaction chamber and is in principle unlimited. Industrially feasible reaction chambers have been found to be those with a ratio of width to height up to a maximum of 5000:1, preferably 1000:1.

The reaction of phosgene with amine in the reaction zone is effected at absolute pressures of at least 0.1 bar to at most 20 bar, preferably of 0.5 bar to 10 bar, more preferably of 0.7 bar to 5 bar.

In a preferred embodiment, the reactor consists of a bundle of reactors. In one possible embodiment, the mixing unit need not be an independent apparatus; instead, it may be advantageous to integrate the mixing unit into the reactor. One example of an integrated unit composed of mixing unit and reactor is that of a tubular reactor with flange-mounted nozzles.

In step (a) according to the invention, the temperature in the reaction zone is preferably selected such that it is above the dissociation temperature of the hydrochlorides of the diamine used, based on the partial pressure conditions which exist in the reaction chamber. According to the amine used and pressure set, an advantageous temperature in the reaction chamber is typically more than 200° C., preferably more than 260° C. and more preferably more than 300° C. In general, the temperature is up to 600 and preferably up to 570° C.

The mean contact time of the reaction mixture in step (a) according to the invention is generally between 0.001 second and less than 5 seconds, preferably of more than 0.01 second to less than 4 seconds, more preferably of more than 0.02 second to less than 3 seconds. "Mean contact time" is understood to mean the period from the commencement of mixing of the reactants until they leave the reaction zone and enter the cooling zone. In a preferred embodiment, the flow in the process according to the invention is characterized by a Bodenstein number of more than 10, preferably more than 100 and more preferably of more than 500.

In a preferred embodiment, the dimensions of the reactor and the flow rates are selected such that a turbulent flow, i.e. a flow with a Reynolds number of at least 2300, preferably at least 2700, for the reaction mixture is present, the Reynolds number being formed with the hydraulic diameter of the reaction chamber.

The gaseous reactants preferably pass through the reaction chamber with a flow rate of 3 to 400 meters/second, preferably of 10 to 250 meters/second. The turbulent flow achieves a narrow residence time with low standard deviation of usually not more than 6%, as described in EP-A 570 799, and good mixing. Measures such as the constriction described in EP-A 593 334, for example, which is additionally prone to blockage, are unnecessary.

In order to build production plants with high plant capacity, it is possible to connect a plurality of reactor tubes in parallel. Corresponding reactor types are known to those skilled in the art. The temperature of the reaction volume, i.e. the reaction zone in the reactor, can be controlled via the outer surface thereof, and the reaction can be conducted isothermally. However, the conversion can also be effected adiabatically. In the case of the adiabatic reaction regime, there is no heat exchange with the environment. This can be accomplished especially by thermal insulation of the reaction zone or of the reactor tubes. The conversion preferably takes place adiabatically. However, intermediate stages of ideally adiabatic and ideally isothermal reaction regime are also possible, in which the abovementioned insulation is designed such that there is still some heat exchange with the environment, or trace heating is optionally provided in order to balance out heat losses.

The conversion in step (a) of the process according to the invention is preferably performed in one stage. This is understood to mean that the mixing and conversion of the reactants proceeds in one step within the desired temperature range. In addition, the process according to the invention is preferably performed continuously.

Step (b)

According to the invention, in step (b), the reaction gases are subsequently cooled in a cooling zone by means of indirect cooling, the cooling medium which absorbs the heat of the reaction gases being conducted in countercurrent to the product stream at least in the region of the highest temperature in the cooling zone.

The term "cooling zone" in the context of step (b) denotes that zone within which the reaction gases are cooled from the temperature at which they leave the reaction zone to a temperature which is below the temperature mentioned. The cooling zone is present within an appropriate cooling apparatus, which thus functions as a heat exchanger.

The term "product stream" denotes the stream of the gaseous products which form in step (a). The latter are referred to as reaction gases.

In the course of step (b), the product stream thus undergoes cooling. The direction of product flow defines the product flow direction. The region of the highest temperature in the cooling zone refers to the temperature of the product stream. The direction of product flow is preferably the same or constant over the entire cooling zone and arises from the geometry of the apparatus in which the cooling takes place. In the case of a cooling zone with a preferably tubular design, the product flow direction arises from the direction of the tube or of the tubes. The product flow direction can change over the course of the cooling zone, for example as a result of deflection of the tubes.

The heat released by the reaction gases is transferred to a heat transfer medium in the course of indirect cooling, i.e. without direct contact with the heat transfer medium, in a heat exchanger. The heat transfer medium is referred to hereinafter as cooling medium. The cooling medium is thus a fluid below the given temperatures, preferably a liquid (cooling liquid).

The cooling medium has to be moved continuously in order to continuously remove the heat. This gives rise to a continuous motion of the cooling medium relative to the product stream. In principle, a cooling medium overall, or parts of the cooling medium, can be conducted in different directions from the product stream or in identical directions to the product stream, for example in cocurrent or in countercurrent to the product stream.

The term "in countercurrent" means, in the context of the present invention, that the cooling medium conducted in countercurrent has the temperature $T_K(x)$ at a first point x in the direction of product flow, and the temperature $T_K(x^*)$ at a second point $x^*$ which is downstream in the product flow, i.e. in flow direction of the product stream, where $T_K(x^*)$ is less than $T_K(x)$. Since the same connection also applies to the temperature of the product stream $T_P$, "in countercurrent" means that the temperature of the cooling medium $T_K$ decreases in product flow direction.

It is also conceivable in principle to divide the stream of the cooling medium into one or more substreams and to implement more than one of the aforementioned flow directions.

According to the invention, however, cooling medium, i.e. at least one substream of the cooling medium, is conducted in countercurrent to the product stream at least in the region of the highest temperature in the cooling zone. Preferably, the entire stream of the cooling medium, in step (b), is conducted in countercurrent direction to the product stream at least in the region of the highest temperature in the cooling zone. Preferably, however, at least one substream and especially all of the cooling medium is conducted in countercurrent direction to the product stream within a region which is responsible for at least 30%, preferably at least 50%, of the lowering of temperature resulting from step (b). Particular preference is given to conducting the stream of the cooling medium in countercurrent direction to the product stream over the entire cooling zone in step (b).

The countercurrent flow can be realized in different ways, for example by a flow regime parallel to the product stream, in which case the cooling medium flows in countercurrent direction, or in a crossed flow regime, in which case the product stream and the stream of the cooling medium cross at particular points. The stream of the cooling medium may alternatively be arranged in spiral form around the product stream. Intermediate stages of the aforementioned implementations are also conceivable.

In a first preferred embodiment, the cooling medium is conducted in countercurrent direction parallel to the product stream (angle 180°). This can be implemented especially by an arrangement of the stream of the cooling medium in the manner of an envelope around the product stream tube(s).

In a second preferred embodiment, the cooling medium is conducted in such a way that it is conducted in spiral form along the product stream in countercurrent direction.

In a third, particularly preferred embodiment, the cooling medium is conducted in crossflow. "Crossflow" is understood to mean that the flow of the cooling medium crosses the flow of the product stream at least two points, the global flow direction of the cooling medium being selected such that the cooling medium flows in countercurrent direction to the product stream. This embodiment can be implemented especially by virtue of the cooling medium crossing the tubes in which the product stream moves (product tubes) at a first contact point, and the cooling medium is then deflected and crosses the product tubes further times downstream in relation to the cooling stream and upstream in relation to the product stream. At the contact points themselves, the angle of the direction of the cooling stream relative to the product stream direction may be 90° or differ from 90°, especially from 60° to 150°, preferably of more than 70° to 140°. The cooling stream can be deflected in the region of the product tubes, i.e. at or close to the product tubes, or outside this region. Very particular preference is given to cooling the reaction gases in step (b) in a tube bundle heat transferer. Tube bundle heat transferers are also known to the person skilled in the art as tube bundle heat exchangers, and enable the described crossflow of the cooling medium. The terms "tube bundle heat transferer" and "tube bundle heat exchanger" should be understood synonymously in the context of the present invention.

The aim of step (b) according to the invention is the sufficiently rapid lowering of the temperature of the products to a temperature at which the formation of by-products or conversion products is avoided. The heat exchanger thus has to enable the cooling to the desired end temperature or intermediate temperature sufficiently rapidly. At the same time, the implementation of the countercurrent principle enables a low or vanishing temperature difference between the temperature of the reaction gases and the temperature of the cooling medium at the inlet point of the reaction gases into the cooling zone and in the rest of the cooling zone.

The cooling in the cooling zone is preferably effected by means of a heat exchanger with a specific heat transfer area of at least 300 $m^2$ per $m^3$ of reaction gas. The specific heat transfer area in the cooling zone is more preferably at least 350 $m^2$ per $m^3$ of reaction gas, especially at least 400 $m^2$ per $m^3$ of reaction gas, most preferably at least 450 $m^2$ per $m^3$ of reaction gas. The upper limit in the specific heat transfer area results from the construction and is, for example, at most 5000 $m^2$ per $m^3$ of reaction gas, especially at most 4000 $m^2$ per $m^3$ of reaction gas.

In principle, useful heat exchangers are those which enable implementation of the countercurrent principle. Suitable heat exchangers are known per se to those skilled in the art. They preferably enable the desired specific heat transfer area of at least 300 $m^2$ per $m^3$ of reaction gas.

Suitable heat exchangers are especially tube bundle heat exchangers, plate heat exchangers and spiral heat exchangers.

The heat exchanger used for the indirect cooling is preferably a tube bundle heat exchanger. A tube bundle heat exchanger enables simple and inexpensive implementation of the preferred specific heat transfer area and of the inventive countercurrent principle.

In one possible embodiment, the temperature at the end of step (b) is less than the temperature of the dew point of the reaction mixture, such that the isocyanate present in the reaction mixture is converted at least partly to the liquid phase as a result of condensation, while phosgene and hydrogen chloride remain essentially completely in the gas phase.

The heat exchanger within which the indirect cooling is effected can thus be designed as a condenser. The indirect cooling can accordingly be effected to such an extent that the isocyanate condenses at least partly in the cooling zone. Any further cooling required can be effected by further downstream cooling stages (see below). Alternatively, it is also possible for cooled but uncondensed reaction gases from step (b) to be supplied to a further cooling stage or directly to a column for low boiler removal.

Preference is given to performing the indirect cooling in step (b) at first up to such a temperature that the isocyanate and any high boilers present in the product stream essentially do not condense. This can effectively prevent the formation of deposits.

The cooling time in step (b) is preferably from 0.01 to 10 seconds, preferably from 0.02 to 5 seconds, especially from 0.05 to 3 seconds. This can effectively prevent the formation of conversion products and by-products. In the context of the present invention, "cooling time" is understood to mean that time which is required to cool the product stream from the temperature at which it enters the cooling zone down to a temperature which is 50° C. above the dew point of the reaction gases.

The cooling zone in step (b), in apparatus terms, can be implemented in different ways. For example, the cooling zone can be implemented in an apparatus separate from the reaction zone. Alternatively, in a second embodiment, the cooling zone can be accommodated together with the reaction zone within one apparatus, which is preferred. In the case of the second, preferred embodiment, the apparatus is preferably a tubular apparatus (flow tube or tubular reactor), in which case the internal tube diameter in the cooling zone differs by at most 50% from the diameter of the reaction zone, more preferably at most 20%, and especially has the same diameter. This can prevent disruption of flow. More particularly, a homogeneous flow through the tube bundle is enabled, such that homogeneous cooling is effected, which in turn further reduces the formation of conversion products. The flow tube mentioned preferably does not comprise any internals which function as baffles.

In a particularly preferred embodiment, the heat transferred by indirect cooling is utilized at least partly for indirect heat transfer to at least one reactant stream of the phosgenation in the gas phase. This is enabled by the high achievable temperature level of the cooling medium in step (b). Processes for indirect heat transfer from a fluid to at least one reactant stream of the phosgenation in the gas phase are known per se to those skilled in the art. In this way, the heat obtained in step (b) can be utilized, and the energy costs of the process can be lowered considerably.

Suitable cooling media are in principle those substances which are liquid and thermally stable within the temperature range required. Preference is given to using a salt melt for indirect cooling. Preferred salt melts are melts of alkali metal nitrates, especially sodium nitrate and/or potassium nitrate.

The cooling in step (b) may be followed by a further cooling stage or optionally a plurality of further cooling stages.

In a preferred embodiment, the cooling in step (b) is followed by at least one further cooling stage (bb). In a second (and further) cooling stage, in the case of direct cooling in stage (bb), the principle of cooling is different, or, in the case of indirect cooling in stage (bb), the particular cooling circuits of steps (b) and (bb) are different from one another.

In the preferred embodiment, in the first cooling stage (b) according to the invention, the reaction gases are cooled in a first cooling zone, the product stream being cooled indirectly by means of a cooling medium in the cooling zone and, as described above, the cooling medium which absorbs the heat of the reaction gases being conducted in countercurrent to the product stream at least in the region of the highest temperature in the cooling zone. In a second stage (bb), the reaction gases are subsequently cooled further in a second cooling zone. The stage (bb) may optionally be followed by further cooling zones and cooling steps (bbb, etc.).

The second cooling stage (bb) may differ in terms of design from the first cooling stage (b), or be performed analogously. For example, it is likewise possible to cool indirectly in the second cooling stage (bb), optionally in countercurrent direction as detailed above. Alternatively, it is possible to cool directly in stage (bb), which is preferred. This allows the formation of deposits to be reduced further.

As already detailed, it is preferred when the product stream is not present in condensed form after step (b). It is, however, preferred when the product stream is at least partly in condensed form after step (bb).

In a particularly preferred embodiment, cooling is effected by means of quenching in step (bb). Direct cooling by means of quenching is known per se to those skilled in the art.

In the course of quenching, the precooled reaction mixture is supplied to a mixing device (quench), in which the temperature of the gas is lowered by introducing a cooler liquid. Embodiments of this process stage may be: wash towers, stirred vessels, bubble columns, quench nozzles and the like. The isocyanate formed can be condensed out (washed out) of the gaseous reaction mixture therein by contact with at least one, preferably exactly one, inert solvent, while excess phosgene, hydrogen chloride and any inert medium pass through this workup apparatus essentially in gaseous form.

The quench liquid must have a good solubility for isocyanates. Preference is given to using organic solvents. In particular, aromatic solvents which may be substituted by halogen atoms are used. Examples of such liquids are toluene, benzene, nitrobenzene, anisole, chlorobenzene, dichlorobenzene (ortho or para or isomer mixtures thereof), trichlorobenzene, 1,3,5-trimethylbenzene (mesitylene), xylene, hexane, diethyl isophthalate (DEIP), tetrahydrofuran (THF), dimethylformamide (DMF) and mixtures thereof, preferably monochlorobenzene.

In a particular embodiment of the process according to the invention, the liquid sprayed in is a mixture of isocyanates, a mixture of isocyanates and solvent, or isocyanate, and the quench liquid used in each case may have fractions of low boilers, such as hydrogen chloride and phosgene. Preference is given to using the isocyanate which is prepared in the particular process. The lowering of the temperature in the quench zone can rule out side reactions with the isocyanates sprayed in. The advantage of this embodiment is especially that a removal of the solvent can be dispensed with.

In an alternative preferred embodiment, the inert medium which is used together with at least one of the reactants, and the solvent which is used in the quench, are the same compound. Very particular preference is given in this case to using monochlorobenzene.

In step (bb), the reaction mixture, which consists essentially of the isocyanates, phosgene and hydrogen chloride, is mixed intensively with the liquid sprayed in. The mixing is effected in such a way that the temperature of the reaction mixture is lowered proceeding from 150 to 250° C. down to 100 to 200° C., preferably down to 100 to 160° C., and the isocyanate present in the reaction mixture is transferred fully or partly by condensation into the liquid droplets sprayed in, while the phosgene and the hydrogen chloride remain essentially completely in the gas phase.

The proportion of the isocyanate present in the gaseous reaction mixture, which is preferably transferred to the liquid phase in the quench zone, is preferably 20 to 100% by weight, more preferably 50 to 99.5% by weight and especially 70 to 99% by weight, based on all of the isocyanate present in the reaction mixture.

The proportion of the phosgene and hydrogen chloride present in the gaseous reaction mixture, which is transferred to the liquid phase in the quench zone, is generally less than 25% by weight, preferably less than 10% by weight.

In order to keep the absorption of phosgene in the quench liquid low in accordance with the invention, the quench is preferably performed at low pressure, for example 1 to 5 bar, and elevated temperature, for example 100 to 160° C.

Particular preference is given to holding the temperature of the inert solvent above the dissolution temperature of the carbamoyl chloride corresponding to the amine in the quench medium.

In principle, for this process stage, it is possible to use all methods and apparatuses which are known per se and are suitable for absorptions, for example a wash column or the spray quenching process. The quenching may be performed in one or more stages, preferably in one stage. The quenching may additionally be implemented in cocurrent or countercurrent mode depending on the process used.

A further suitable quench is known, for example, from EP-A 1 403 248, column 2 line 39-column 3 line 18, to which explicit reference is made in the context of this disclosure. In addition, the quenching can be performed according to the details in WO 2008/055899, WO 2008/055904 or WO 2005/123665, to which full reference is hereby made.

The reaction mixture flows through the quench zone, preferably from the top downward. Below the quench zone is arranged a collecting vessel in which the liquid phase is precipitated, collected and removed via an outlet, and then worked up. The remaining gas phase is removed via a second outlet from the collecting vessel and likewise worked up.

Small amounts of by-products which remain in the isocyanate can be separated from the desired isocyanate especially by means of additional rectification, by stripping with an inert gas or by crystallization, preferably by rectification.

Workup

After step (b) and optionally further cooling stages (bb, etc.), the isocyanate is optionally worked up in a step (c) to remove by-products and unreacted reactants, which include especially the evaporation of the phosgene and hydrogen chloride remaining in the condensed phase.

Corresponding processes for working up the isocyanate are known to those skilled in the art. The person skilled in the art selects one or more suitable workup processes depending on the temperature and the phase state of the reaction products, which also depends on the type of cooling which was last employed.

In a preferred embodiment, the isocyanate is removed from the solvent by distillation and more preferably by rectification. It is likewise possible here to remove residual impurities comprising hydrogen chloride, inert medium and/or phosgene, as described, for example, in DE-A 10260092.

In step (c), gaseous streams which consist essentially of phosgene and/or hydrogen chloride gas, with or without inert medium, are obtained. Hydrogen chloride is removed from the phosgene in a manner known per se to those skilled in the art in at least some of these streams comprising phosgene and/or hydrogen chloride gas and/or inert medium.

In a further preferred embodiment, the removal is effected in such a way that the mass fraction of hydrogen chloride in the phosgene-containing stream after any mixing performed with fresh phosgene, before the mixing with the amine-containing stream, is less than 15% by weight, preferably less than 10%, and more preferably less than 5% by weight.

The mixture comprising hydrogen chloride and/or phosgene and any solvent from the quench is preferably separated by means of distillation and/or scrubbing. Preference is given to performing the separation in a combination of a distillation and a scrubbing.

The scrubbing medium may especially be toluene, benzene, nitrobenzene, anisole, chlorobenzene, dichlorobenzene (ortho or para or isomer mixtures thereof), trichlorobenzene, xylene, hexane, diethyl isophthalate (DEIP), tetrahydrofuran (THF), dimethylformamide (DMF) and mixtures thereof, preferably monochlorobenzene. Particular preference is given to using, as the scrubbing liquid, the same solvent as in step (bb) in the quenching. The scrubbing can be effected in cocurrent or preferably in countercurrent.

In the case of a combined scrubbing and distillation, for example a pressure distillation, phosgene is scrubbed out of the hydrogen chloride-containing stream by scrubbing with a scrubbing medium, preferably toluene, chlorobenzene or dichlorobenzene. In an exceptional case, phosgene is present here in condensed form. The removal of phosgene and hydrogen chloride from the laden scrubbing medium after the scrubbing is effected preferably by distillation or by desorption. The removal is preferably effected so as to obtain a gaseous phosgene stream which, in a particularly preferred embodiment, optionally after mixing with fresh phosgene, comprises a hydrogen chloride content of less than 15% by weight.

The scrubbing and the distillation are conducted at pressures of 1 to 10 bar absolute, preferably of 1 to 5 bar absolute.

The hydrogen chloride/phosgene separation may be followed downstream by an adsorption unit, preferably an activated carbon filter, in the hydrogen chloride stream removed from the separation, in which traces of the scrubbing medium can be removed from the hydrogen chloride obtained.

Subsequently, in an optional embodiment, the stream which comprises predominantly phosgene and is thus obtained is recycled as a feedstock in the process according to the invention.

A preferred embodiment of the present invention is illustrated schematically in FIG. 1. FIG. 1 serves to explain this preferred embodiment of the present invention and should not be interpreted in a restricted manner. Individual elements of the preferred embodiment explained below can advantageously be combined with embodiments explained above.

Key for FIG. 1:

1 Reaction zone
2 Reactor
3 Cooling apparatus
4 Cooling fluid flow
5 Product stream
6 Reactant stream
7 Mixing apparatus
8 Amine stream
9 Heating apparatus
10 Phosgene stream
11 Cooling stream
12 Cooling zone
13 Optional supplementary heat source Description of the preferred embodiment according to FIG. 1:

The reactant stream (6) comprising at least one amine and phosgene enters the reaction zone (1) which is within a reactor (2). Subsequently, the resulting gas stream (product stream (5)) enters the cooling zone (12) which is within the cooling apparatus (3), which is preferably a tube bundle heat transferer (tube bundle heat exchanger).

The product stream (5) is cooled by means of a cooling stream (11) which flows in countercurrent direction to the direction of the product stream (5) within the cooling fluid flow (4), the cooling fluid flow (4) within the cooling apparatus (3) preferably being implemented in the form of deflecting devices within a tube bundle heat transferer, especially deflecting plates. In the preferred embodiment, the cooling stream crosses the product stream at several points (crossed configuration, see above). The product stream (5) subsequently leaves the region of indirect cooling. The heated cooling stream (11) is optionally heated further by means of an optional supplementary heat source (13) and is subsequently used to heat the amine stream (8) in a heating apparatus (9). The optional supplementary heat source (13) may especially be an electrical heating apparatus or a heat exchanger which operates with combustion gases.

The heated amine stream (8) leaves the heating apparatus (9) and is heated further by means of an optional supplementary heat source (13). Any optional supplementary heat source (13) implemented after preheating of the amine stream (8) can, as explained above, be designed especially as an electrical heating apparatus or as a heat exchanger which operates with combustion gases. Subsequently, the preheated amine stream (8), and likewise the phosgene stream (10), enters the mixing apparatus (7). The mixing apparatus (7) may be an apparatus separated from the reactor (2), or may be integrated into the reactor (2).

The invention claimed is:

1. A process for preparing isocyanates, comprising
    (a) the reaction of at least one amine with phosgene in the gas phase in a reaction zone and
    (b) the subsequent cooling of the reaction gases, from the temperature at which the reaction gases leave the reaction zone to a temperature which is below the temperature at which the reaction gases leave the reaction zone, in a cooling zone by means of indirect cooling, the cooling medium which absorbs the heat of the reaction gases being conducted in countercurrent to the product stream at least in the region of the highest temperature in the cooling zone,
    wherein the cooling is from the temperature at which the reaction gases enter the cooling zone down to a temperature which is 50° C. above the dew point of the reaction gases, with a cooling time of from 0.01 to 10 seconds, and wherein the heat absorbed by the cooling medium in step (b) is utilized at least partly for indirect heat transfer to at least one reactant stream of the reaction in step (a).

2. The process according to claim 1, wherein the cooling in step (b) is performed in a heat exchanger with a specific heat transfer area of at least 300 m2 per m3 of reaction gas.

3. The process according to claim 2, wherein the heat exchanger is a tube bundle heat exchanger.

4. The process according to claim 1, wherein the cooling time in step (b) is from 0.1 to 5 seconds.

5. The process according to claim 1, wherein the isocyanate is not present in condensed form in the course of step (b).

6. The process according to claim 1, wherein the reaction zone in step (a) and the cooling zone in step (b) are within one apparatus which is tubular.

7. The process according to claim 1, wherein the cooling in step (b) is followed, as step (bb), by a further cooling of the reaction gases.

8. The process according to claim 7, wherein the cooling in steps (b) and (bb) is in each case performed indirectly, and wherein the cooling media in steps (b) and (bb) are within different circuits.

9. The process according to claim 7, wherein the reaction gases are cooled directly in step (bb).

10. The process according to claim 9, wherein cooling is effected by means of quenching in step (bb).

11. The process according to claim 1, wherein the cooling medium which absorbs the heat of the reaction gases is a salt melt.

12. The process according to claim 1, wherein the amine used is at least one aromatic diamine having from 6 to 18 carbon atoms or at least one (cyclo)aliphatic diamine having from 2 to 18 carbon atoms.

13. The process according to claim 1, wherein the amine used is at least one selected from toluenediamines.

14. The process according to claim 1, wherein the amine used is at least one selected from diaminodiphenylmethanes.

15. The process according to claim 1, wherein the amine used is at least one aliphatic diamine having from 2 to 18 carbon atoms.

16. The process according to claim 13, wherein the amine used is toluene-2,4-diamine.

17. The process according to claim 13, wherein the amine used is toluene-2,6-diamine.

18. The process according to claim 14, wherein the amine used is 4,4'-diamino-diphenylmethane, 2,4'-diaminodiphenylmethane or 2,2'-diaminodiphenylmethane.

19. The process according to claim 15, wherein the amine used is hexamethylene-1,6-diamine.

* * * * *